US008497975B2

(12) United States Patent
De Wit et al.

(10) Patent No.: US 8,497,975 B2
(45) Date of Patent: Jul. 30, 2013

(54) INSPECTION METHOD AND APPARATUS, LITHOGRAPHIC APPARATUS, LITHOGRAPHIC PROCESSING CELL AND DEVICE MANUFACTURING METHOD

(75) Inventors: Johannes Matheus Marie De Wit, Helmond (NL); Armand Eugene Albert Koolen, Nuth (NL)

(73) Assignee: ASML Netherlands B.V.

( * ) Notice: Subject to any disclaimer, the term of this patent is extended or adjusted under 35 U.S.C. 154(b) by 318 days.

(21) Appl. No.: 12/795,595

(22) Filed: Jun. 7, 2010

(65) Prior Publication Data
US 2010/0315613 A1 Dec. 16, 2010

Related U.S. Application Data

(60) Provisional application No. 61/186,217, filed on Jun. 11, 2009.

(51) Int. Cl.
*G03B 27/68* (2006.01)

(52) U.S. Cl.
USPC ............................ 355/52; 355/67; 355/77

(58) Field of Classification Search
USPC ............... 355/50, 52, 53, 55, 67, 68, 77
See application file for complete search history.

(56) References Cited

U.S. PATENT DOCUMENTS

| 4,888,614 A * | 12/1989 | Suzuki et al. ................ 355/43 |
| 5,479,238 A * | 12/1995 | Whitney ........................ 355/53 |
| 5,831,715 A * | 11/1998 | Takahashi ..................... 355/53 |
| 6,721,259 B1 * | 4/2004 | Yamamoto et al. ...... 369/112.26 |
| 2004/0160653 A1 * | 8/2004 | Falk ............................. 358/519 |
| 2006/0028927 A1 * | 2/2006 | Wada et al. ................ 369/30.03 |
| 2006/0109483 A1 * | 5/2006 | Marx et al. .................. 356/609 |
| 2006/0209298 A1 * | 9/2006 | Kvamme et al. .......... 356/237.2 |
| 2009/0092010 A1 | 4/2009 | Kujper et al. |
| 2010/0079748 A1 | 4/2010 | Ryzhikov |
| 2010/0315613 A1 * | 12/2010 | De Wit et al. .................. 355/67 |

FOREIGN PATENT DOCUMENTS

| EP | 1 043 615 A1 | 10/2000 |
| EP | 1 628 164 A2 | 2/2006 |
| EP | 2 169 466 A1 | 3/2010 |

OTHER PUBLICATIONS

International Search Report mailed Oct. 6, 2010 for International Application No. PCT/EP2010/057769, 4 pgs.
International Preliminary Report on Patentability and Written Opinion of the International Searching Authority directed to related International Patent Application No. PCT/EP2010/057769, mailed Dec. 12, 2011; 8 pages.

* cited by examiner

*Primary Examiner* — Thomas R Artman
(74) *Attorney, Agent, or Firm* — Sterne, Kessler, Goldstein & Fox P.L.L.C.

(57) ABSTRACT

A scatterometer configured to derive a property of a substrate, includes an optical arrangement that produces a beam of radiation. An objective lens is arranged to focus the beam of radiation onto a target on the substrate. The optical arrangement is arranged to change the divergence of the beam incident on the objective lens, thereby changing spherical aberration caused by the objective lens on the beam focused on the target. A detection arrangement is arranged to detect the beam of radiation after reflection or scattering from the substrate.

15 Claims, 5 Drawing Sheets

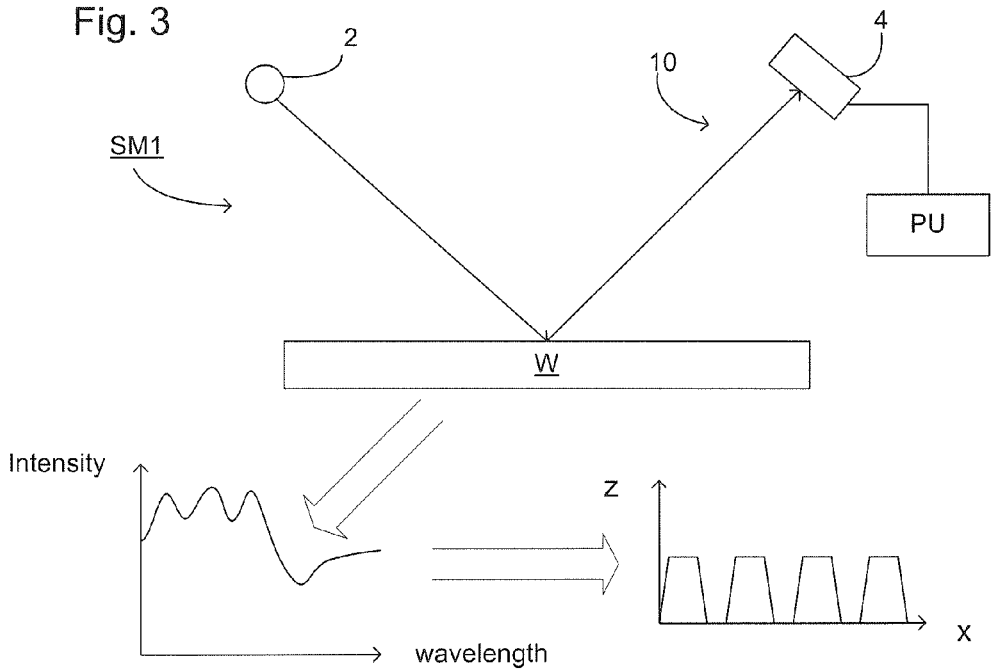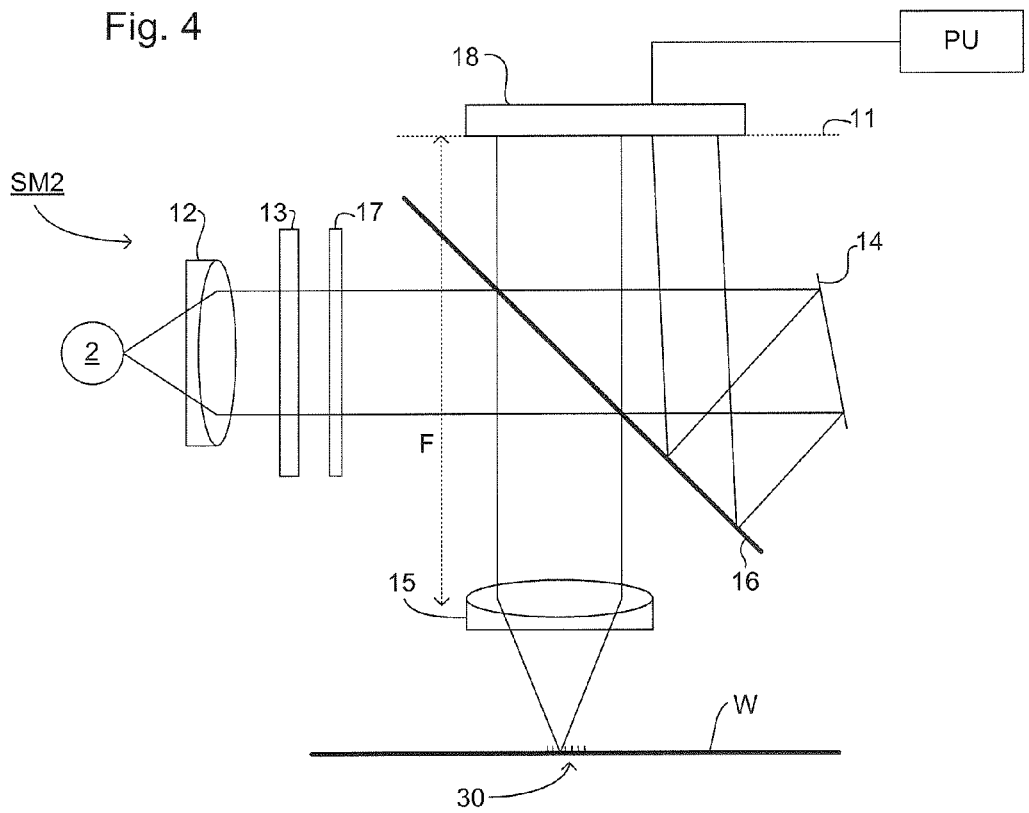

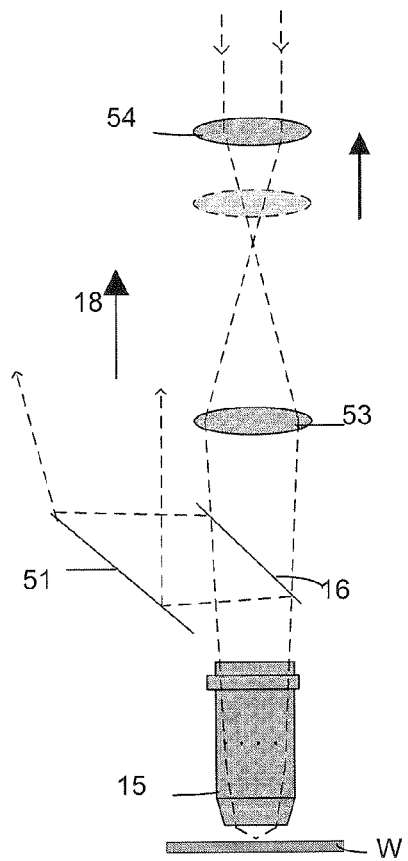
Fig. 8
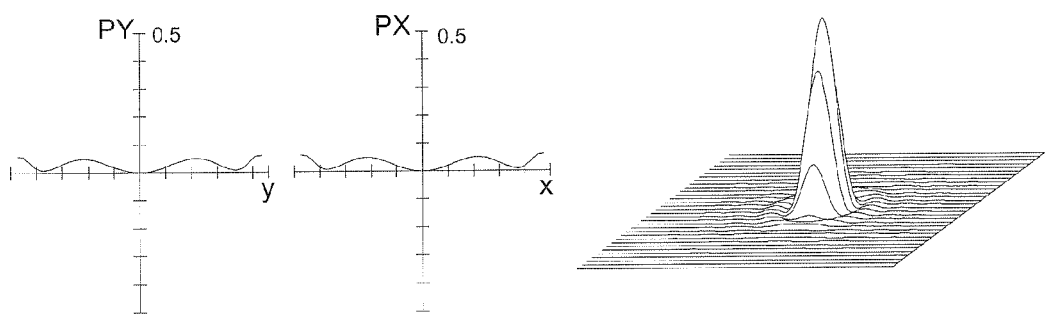
Fig. 9
Fig. 10

INSPECTION METHOD AND APPARATUS, LITHOGRAPHIC APPARATUS, LITHOGRAPHIC PROCESSING CELL AND DEVICE MANUFACTURING METHOD

CROSS REFERENCE TO RELATED APPLICATIONS

This application claims the benefit under 35 U.S.C. §119 (e) to U.S. Provisional Patent Application 61/186,217 filed Jun. 11, 2009, which is incorporated herein by reference in its entirety.

BACKGROUND

1. Field of the Invention

The present invention relates to methods of inspection usable, for example, in the manufacture of devices by lithographic techniques and to methods of manufacturing devices using lithographic techniques.

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is necessary to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

In either a spectroscopic scatterometer or an angularly resolved scatterometer an objective lens is used to direct a beam of radiation on to the substrate. The radiation reflected from the substrate, then passes back through the objective lens, to be split from the incident radiation to pass towards a detector arrangement. However, the objective lens incorporated in such scatterometers is generally designed to be used for visible light, which is wavelengths between about 450 and 700 nm. In a scatterometer, it is advantageous to be able to use radiation of smaller wavelengths, for example about 400 nm. At such wavelengths however, particularly for angularly resolved scatterometers for which the numerical aperture of the objective lens is relatively large, chromatic aberration, in particular spherical aberration, exhibited by the objective lens becomes significant and the shape of the radiation spot on the substrate is not diffraction limited, leading to errors in the properties of the substrate determined from the reflected beam.

SUMMARY

It is desirable to provide a scatterometer which may take account of characteristics of an objective lens at differing radiation wavelengths.

According to a first embodiment of the invention, there is provided an inspection apparatus configured to derive a property of a substrate. An optical arrangement is configured to produce a beam of radiation. An objective lens arrangement is configured to focus the beam of radiation on the substrate. A detection arrangement is configured to detect the beam of radiation after reflection or scattering from the substrate. The optical arrangement is arranged to change the divergence of the beam of radiation incident on the objective lens arrangement, so as to cause a corresponding change in the spherical aberration caused by the objective lens arrangement on the beam of radiation focused on the substrate.

According to a second embodiment of the invention there is provided a method of deriving a property of a substrate, comprising the following steps. Producing a beam of radiation. Focusing the beam of radiation on the substrate using an objective lens arrangement. Changing the divergence of the beam of radiation incident on the objective lens arrangement, so as to cause a corresponding change in spherical aberration in the beam of radiation focused on the substrate. Detecting the beam of radiation after reflection or scattering from the substrate. Using the detected beam to derive the property of the substrate.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

FIG. 1 depicts a lithographic apparatus.
FIG. 2 depicts a lithographic cell or cluster.
FIG. 3 depicts a first scatterometer.
FIG. 4 depicts a second scatterometer.

FIG. 8 illustrates part of the optical system of a scatterometer in accordance with an embodiment of the present invention.

FIG. 9 illustrates the variation in wave front error across the wafer in the scatterometer of FIG. 8.

FIG. 10 illustrates the Huygens point spread function of the radiation spot produced by the optical system illustrated in FIG. 8.

Figure 1:
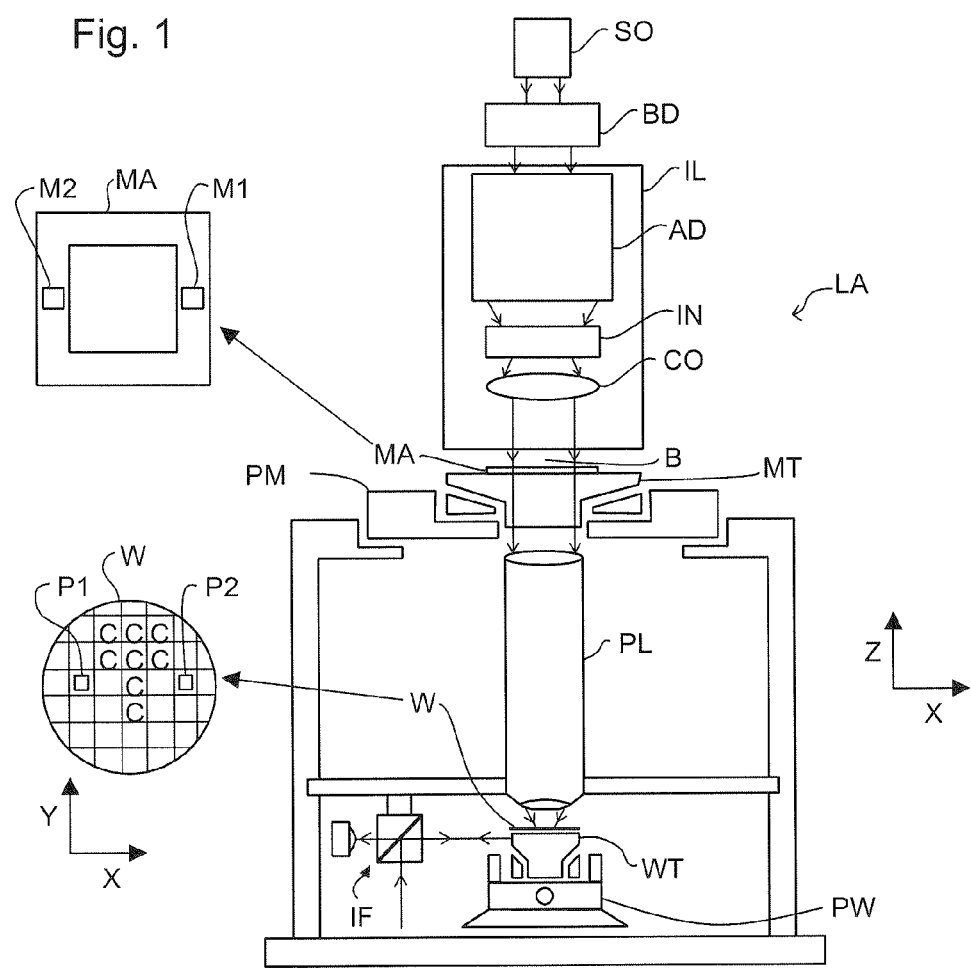

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts a lithographic apparatus. The apparatus comprises an illumination system (illuminator) IL configured to condition a radiation beam B (e.g., UV radiation or DUV radiation); a support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist-coated wafer) W and connected to a second positioner PW configured to accurately position the substrate in accordance with certain parameters; and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as a-outer and a-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
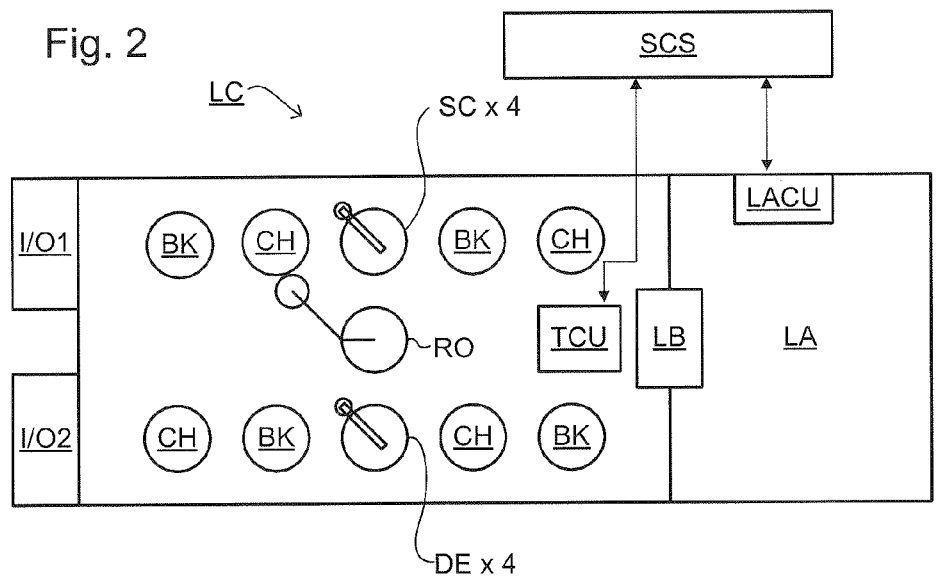

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be perfoiined only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist, which have been exposed to radiation, and those that have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

FIG. 3 depicts a scatterometer SM1 which may be used in the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another scatterometer SM2 that may be used with the present invention is shown in FIG. 4. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\Delta 8$ and a spacing of at least $2\Delta 8$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

Figure 5:
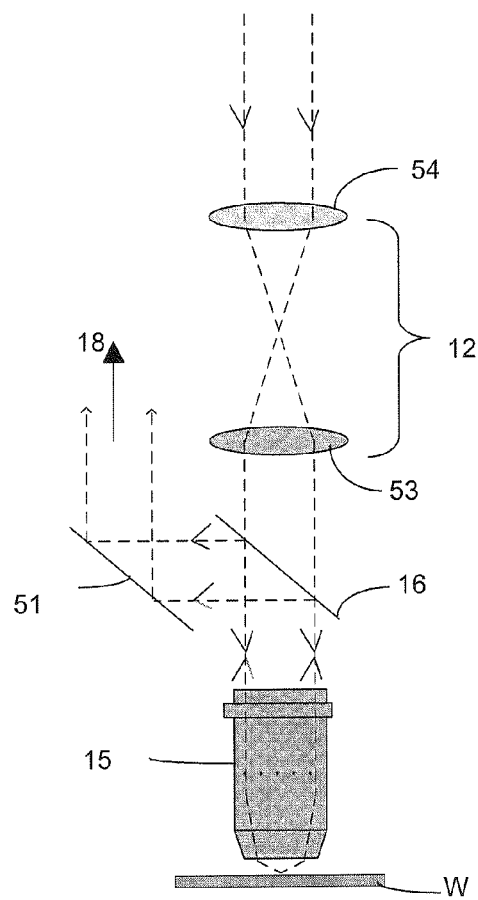
FIG. 5 illustrates part of an optical system incorporated in a scatterometer not in accordance with the invention.

Referring to FIG. 5, this figure shows a detail of the optical system which may be incorporated in a scatterometer of the type shown in FIG. 4, according to an embodiment of the present invention. In the particular optical system configuration illustrated in FIG. 5, a further reflective surface 51 has been provided, which is effective to direct the reflected radiation towards the detector 18, for example a CCD camera. The illumination optics 12 is constituted by two lenses 53, 54 which are effective to project a collimated beam through the partially reflective surface 16, to pass through the objective lens 15, which is effective to focus a radiation spot onto the wafer W.

Figure 6:
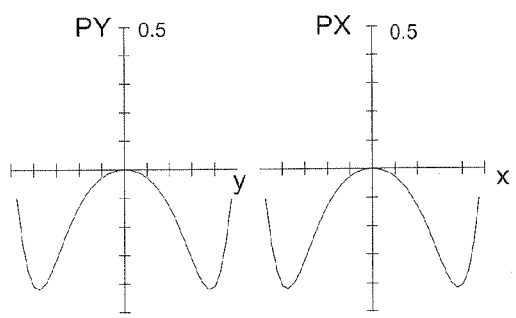
FIG. 6 illustrates the variation in the wave front error across the wafer in the scatterometer shown in FIG. 5.
Figure 7:
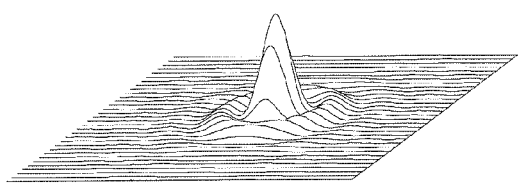
FIG. 7 illustrates the Huygens point spread function across the wafer of the radiation spot produced by the optical system illustrated in FIG. 5.

Referring now to FIGS. 6 and 7, which show an embodiment of the present invention, a scatterometer will usually incorporate an objective lens system 15 that has been designed for use with visible radiation, typically in the wavelength 550 nm. In one example, at 400 nm chromatic aberration, mainly spherical aberration, of the objective lens becomes noticeable such that the radiation spot on the wafer W is not diffraction limited. This will give a typical wavefront error as shown in FIG. 6, which has been measured at a wavelength of 400 nm. As can be seen from this figure, in which the vertical scale represents an optical path difference, PX or PY, of ±0.5 Waves, and the horizontal scale represents the distance to the optical axis in the x or y directions, there is a maximum wave front error of up to 0.468 Waves in both the PX and PY directions, with an rms wave front error of 0.140 Waves. In order for the spot produced by the objective lens 15 to be diffraction limited, the rms wave front error should be less than 0.070 Waves.

FIG. 7 illustrates the Huygens point spread function for the optical system illustrated in FIG. 5, again for the wavelength of 400 nm, according to an embodiment of the present invention. From this function it can be shown that the Strehl ratio, i.e., the ratio of the observed peak intensity at the detection plane from a point source, compared to the theoretical maximum peak intensity of a perfect imaging system working at the diffraction limit, is only about 0.48 indicating that a lot of the radiation energy is outside the Airy disc of the objective lens 15. Because of these large wave front errors and pole spot shapes, calculation of the grating and stack properties derived from the measured scatterometer spectra can have errors.

In one example, it is possible to adjust the amount of spherical aberration by adjustment of the divergence of the beam of radiation incident on the objective lens. In particular, in accordance with an embodiment of the invention, the optics of the scatterometer is modified to enable the radiation beam to be convergent prior to reaching the objective lens and passing through the objective lens onto the wafer. In one example, such an arrangement results in fewer spherical aberrations in the objective lens system for low wavelength radiation of 400 nm and slightly more spherical aberrations for higher wavelengths. By careful adjustment of the scatterometer parameters, however, spherical aberrations at all wavelengths can be kept within acceptable limits for the scatterometer. Convergence of the beam may be produced in different ways, for example by positioning of the lenses in the illumination system or by the insertion of an extra lens.

Turning now to FIG. 8, this figure illustrates part of the illumination system for a scatterometer, in accordance with an embodiment of the invention. In the particular embodiment illustrated, the lens 54 illustrated in FIG. 5 has been moved from the dotted position in the direction of the arrow shown in FIG. 8, such that the beam produced by the illumination system 12 incident on the objective lens 15 is a convergent beam.

Turning now to FIGS. 9 and 10, these figures illustrate equivalent measurement to those shown in FIGS. 6 and 7 for the optical system illustrated in FIG. 8, again for measurements at 400 nm. As can be seen from FIG. 9, the wave front errors are significantly reduced compared to those shown in FIG. 6. In particular the maximum wave front error is 0.08 waves with an rms wave front error of 0.18 Waves. It can be calculated from FIG. 10, that the Strehl ratio is 0.988, indicating that the profile of the radiation spot on the wafer W is diffraction limited. By such an arrangement it is possible to use the scatterometer to give grating and stack property derivations of high accuracy.

In the particular embodiment described above, the level of spherical aberration produced in the radiation spot formed on the wafer W can be reduced by making the beam incident on the objective lens convergent, in such a way that the objective lens can be used over a broader wavelength range, for example from 400 to 700 nm, compared to the 450 to 700 nm which would otherwise be possible. It will be appreciated that by making the beam incident on the objective lens divergent, the scatterometer can be made suitable for use at longer wavelengths than would otherwise be possible, for example in the range 450 to 750 or 800 nm, rather than the range 450 to 700 nm that would otherwise be possible.

It will also be appreciated that in an alternative embodiment of the invention, the optical system for the scatterometer may be constructed including a moveable lens, such that the divergence of the beam incident on the objective lens may be varied, dependent on the wavelength of the incident beam, enabling optimization of the spherical aberration produced by the objective lens at any wavelength.

Figure 11:
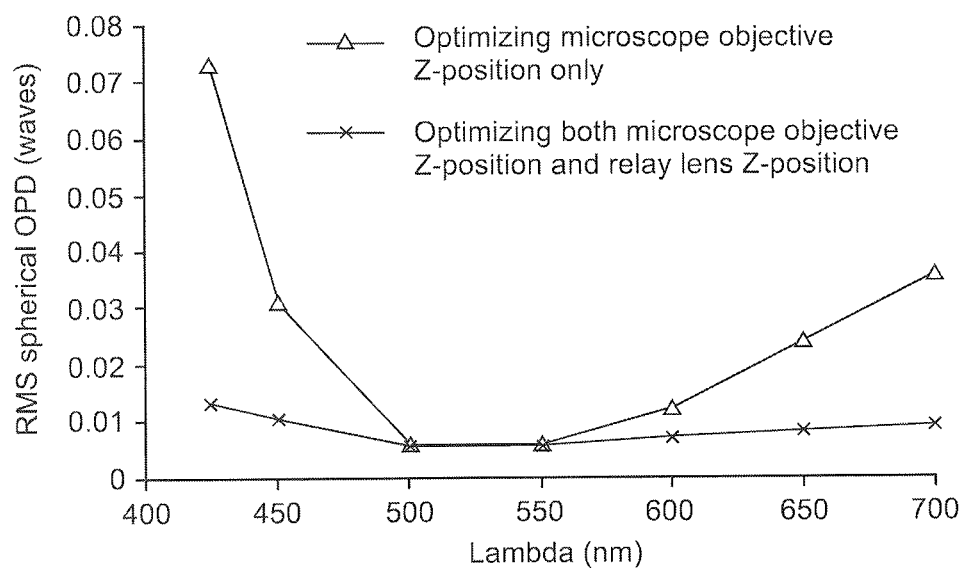
FIG. 11 illustrates the root mean square (RMS) spherical optical path difference (OPD) performance achieved by optimizing the microscope objective Z-position and by optimizing simultaneously the microscope objective Z-position and the relay lens Z-position in the optical system.

In another embodiment of the invention, the level of spherical aberration produced in the radiation spot formed on the wafer W can be dramatically decreased by simultaneous movement of lens 53 or lens 54 and microscope objective 15. FIG. 11, according to an embodiment of the present invention, illustrates firstly the RMS spherical OPD that can be achieved by optimizing the Z-position of the microscope objective alone. FIG. 11 also illustrates, for the purpose of comparison, the RMS spherical OPS that can be achieved by simultaneously optimizing the Z-position of the microscope objective 15 and the Z-position of the lens 53 or 54. The simultaneous optimization of the Z-positions of the microscope objective 15 and the lens 53 or 54 clearly provides improved performance over a wider wavelength range; accordingly extending the useful wavelength range of such an illumination system.

In addition to minimizing the RMS spherical OPD achieved by the illumination system, the simultaneous optimization of microscope objective 15 and lens 53 or 54 can be used to compensate for additional spherical aberrations that may be incurred by probing through thick optical layers covering the target on the wafer W. Thus, the simultaneous optimization of the Z-positions of the microscope objective 15 and the lens 53 or 54 allows the same illumination system to adaptively compensate for thick optical covering layers in addition to the above-mentioned benefits.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

Conclusion

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An inspection apparatus configured to derive a property of a substrate, comprising:
   an optical arrangement configured to produce a beam of radiation;
   an objective lens arrangement configured to focus the beam of radiation on the substrate; and
   a detection arrangement configured to detect the beam of radiation after reflection or scattering from the substrate,
   wherein the optical arrangement and the objective lens arrangement are arranged such that a simultaneous movement of the optical arrangement and the objective lens arrangement changes divergence of the beam of radiation incident on the objective lens arrangement, so as to cause a corresponding change in a spherical aberration caused by the objective lens arrangement on the beam of radiation focused on the substrate.

2. The inspection apparatus according to claim 1, wherein the optical arrangement comprises at least one lens arranged along an optical axis of the apparatus.

3. The inspection apparatus according to claim 2, wherein the position along the optical axis of the at least one lens is variable so as to enable the divergence of the beam of radiation to be varied.

4. The inspection apparatus according to claim 2 wherein the position along the optical axis of the at least one lens and the position of the objective lens arrangement are variable so as to reduce the spherical aberration within the range of wavelengths at which the inspection apparatus operates.

5. The inspection apparatus according to claim 2 wherein the position along the optical axis of the at least one lens and the position of the objective lens arrangement are variable so as to compensate for spherical aberration caused by optical layers on the substrate within the range of wavelengths at which the inspection apparatus operates.

6. The inspection apparatus according to claim 1, wherein the optical arrangement is arranged to cause the beam of radiation incident on the objective lens arrangement to be convergent so as to reduce the spherical aberration at lower wavelength ranges within the range of wavelengths at which the inspection apparatus operates.

7. The inspection apparatus according to claim 1, wherein the optical arrangement is arranged to cause the beam of radiation incident on the objective lens arrangement to be divergent so as to reduce the spherical aberration at higher wavelength ranges within the range of wavelengths at which the inspection apparatus operates.

8. A method of deriving a property of a substrate, comprising:
   producing a beam of radiation using an optical arrangement;
   focusing the beam of radiation on the substrate using an objective lens arrangement;
   simultaneously moving the optical arrangement and the objective lens arrangement to change a divergence of the beam of radiation incident on the objective lens arrangement, so as to cause a corresponding change in spherical aberration in the beam of radiation focused on the substrate;
   detecting the beam of radiation after reflection or scattering from the substrate; and
   using the detected beam to derive the property of the substrate.

9. The method according to claim 8, wherein the beam is produced by one or more lenses of the optical arrangement arranged along an optical axis, the relative positions of the one or more lenses along the optical axis being adjusted, such that the plurality of lenses produce the beam.

10. The method according to claim 9, wherein the position along the optical axis of at least one of the one or more lenses and the position of the objective lens arrangement are adjusted so as to reduce the spherical aberration within the range of wavelengths used in the method.

11. The method according to claim 9, wherein the position along the optical axis of at least one of the one or more lenses and the position of the objective lens arrangement are adjusted so as to compensate for spherical aberration caused by optical layers on the substrate within the range of wavelengths used in the method.

12. The method according to claim 8, wherein the beam of radiation incident on the objective lens arrangement is caused to he convergent so as to reduce the spherical aberration at lower wavelength ranges within a range of wavelengths.

13. The method according to claim 8, wherein the beam of radiation incident on the objective lens arrangement is caused to he divergent so as to reduce the spherical aberration at higher wavelength ranges within the range of wavelengths, 14. A lithographic apparatus comprising:
an illumination optical system arranged to illuminate a pattern of a patterning device;
a projection optical system arranged to project an image of the pattern on to a substrate; and
an inspection apparatus comprising,
an optical arrangement configured to produce a beam of radiation;
an objective lens arrangement configured to focus the beam of radiation on the substrate; and
a detection arrangement configured to detect the beam of radiation after reflection or scattering from the substrate,
wherein the optical arrangement and the objective lens arrangement are arranged such that a simultaneous movement of the optical arrangement and the objective lens arrangement changes divergence of the beam of radiation incident on the objective lens arrangement, so as to cause a corresponding change in a spherical aberration caused by the objective lens arrangement on the beam of radiation focused on the substrate.

15. A lithographic cell comprising:
a coater arranged to coat a substrate with a radiation sensitive layer;
a lithographic apparatus arranged to expose images onto the radiation sensitive layer of the substrate coated by the coater;
a developer arranged to develop images exposed by the lithographic apparatus; and
an inspection apparatus comprising,
an optical arrangement configured to produce a beam of radiation;
an objective lens arrangement configured to focus the beam of radiation on the substrate; and
a detection arrangement configured to detect the beam of radiation after reflection or scattering from the substrate,
wherein the optical arrangement and the objective lens arrangement are arranged such that a simultaneous movement of the optical arrangement and the objective lens arrangement changes change divergence of the beam of radiation incident on the objective lens arrangement, so as to cause a corresponding change in a spherical aberration caused by the objective lens arrangement on the beam of radiation focused on the substrate.

* * * * *

UNITED STATES PATENT AND TRADEMARK OFFICE
CERTIFICATE OF CORRECTION

| | | |
|---|---|---|
| PATENT NO. | : 8,497,975 B2 | Page 1 of 1 |
| APPLICATION NO. | : 12/795595 | |
| DATED | : July 30, 2013 | |
| INVENTOR(S) | : Johannes Matheus Marie De Wit | |

It is certified that error appears in the above-identified patent and that said Letters Patent is hereby corrected as shown below:

In the Claims:

Column 13, in claim 12, line 17, please delete "he" and replace with "be"
Column 13, in claim 13, line 21, please delete "he" and replace with "be"
Column 13, in claim 13, line 22, please delete "," and replace with "."

Signed and Sealed this
Twenty-eighth Day of January, 2014

Michelle K. Lee
*Deputy Director of the United States Patent and Trademark Office*